(12) United States Patent
Tarumi et al.

(10) Patent No.: US 7,537,688 B2
(45) Date of Patent: May 26, 2009

(54) BLOOD PURIFICATION DEVICE

(75) Inventors: Masatoshi Tarumi, Haibara-gun (JP);
Yoshihiro Mori, Haibara-gun (JP);
Masahiro Toyoda, Haibara-gun (JP);
Tomoya Murakami, Haibara-gun (JP)

(73) Assignee: Nikkiso Co., Ltd., Tokyo (JP)

( * ) Notice: Subject to any disclaimer, the term of this patent is extended or adjusted under 35 U.S.C. 154(b) by 711 days.

(21) Appl. No.: 11/209,278

(22) Filed: Aug. 22, 2005

(65) Prior Publication Data
US 2006/0043007 A1     Mar. 2, 2006

(30) Foreign Application Priority Data
Aug. 24, 2004  (JP)  ............................. 2004-244220
May 23, 2005  (JP)  ............................. 2005-149861

(51) Int. Cl.
*B01D 61/30*     (2006.01)
*A61M 1/14*      (2006.01)

(52) U.S. Cl. ................... 210/96.2; 210/321.6; 604/6.08; 604/6.09

(58) Field of Classification Search ............... 210/96.2, 210/321.6; 604/6.09, 6.08
See application file for complete search history.

(56) References Cited

U.S. PATENT DOCUMENTS 6,537,240 B2     3/2003     Cavicchioli et al.

7,381,195 B2 *   6/2008     Mori et al. ............... 604/6.08

FOREIGN PATENT DOCUMENTS

| JP | 11226119 A | * | 8/1999 |
| JP | 2000-502940 | | 3/2000 |
| JP | 2004097782 A | * | 4/2004 |

* cited by examiner

*Primary Examiner*—Terry K Cecil
(74) *Attorney, Agent, or Firm*—Darby & Darby P.C.

(57) ABSTRACT

A blood purification device confirms whether a specific peak is provided by e.g. an ultrafiltration pump, to concentrate the blood or not and also accurately measures a blood re-circulation with a minimum of parameters providing a ratio of re-circulating blood. The blood purification device composed of arterial blood circuit route $1a$ and venous blood circuit route $1b$, blood pump 3, dialyzer 2, water removal pump 8 providing the specific peak in the variation of blood concentration by removing water rapidly, and a detector detecting the specific peak, can measure the blood re-circulation thereby. The re-circulating blood flowing is the blood which was introduced again to arterial blood circuit route $1a$ after it had been returned to a patient from venous blood circuit route $1b$. A first detector $5a$ installed in the arterial blood circuit route $1a$ and a second detector $5b$ installed in venous blood circuit route detector.

7 Claims, 3 Drawing Sheets

BLOOD PURIFICATION DEVICE

INCORPORATION BY REFERENCE

The present application claims priority under 35 U.S.C. § 119 to Japanese Patent Application Nos. 2004-244220 filed on Aug. 24, 2004 and 2005-149861 filed May 23, 2005. The contents of the applications are incorporated herein by reference in their entireties.

FIELD OF THE INVENTION

The present invention relates to a blood purification device which purifies blood from a patient in extracorporeal blood circulation.

BACKGROUND OF THE INVENTION

In general, purification treatment such as dialysis treatment, a blood circuit route consisting of flexible tubing is used to place the blood of patient in extracorporeal circulation. This blood circuit route arrangement mainly includes an arterial blood circuit route having an arterial needle at one end to collect blood from the patient and a venous blood circuit route having a venous needle at the other end to return the blood to the patient. A dialyzer between the arterial blood circuit route and the venous blood circuit route purifies the blood circulating extracorporeally.

Such a dialyzer includes plural hollow fibers in the inside of dialyzer. Blood flows in each inside hollow fiber and dialysis fluid flows outside the hollow fibers (i.e. between external surface face of the hollow fiber and inside surface face of the dialysis device case). The hollow fiber is a blood purification membrane with small pores on its surface. Wastes in the blood flowing in the inside of hollow fiber are discharged into the dialysis fluid after passing through the blood purification membrane, and the blood, of which wastes are discharged for purification, returns to the patient. Also a ultrafiltration pump installed in the inside of the dialysis device removes water from patient's blood while dialyzing the patient.

When, for instance, the arterial needle and the venous needle are punctured to the shunt (a connected part of an artery and a vein by a surgical operation) and its periphery to circulate the blood extracorporeally, a blood-recirculation takes place by which the blood purified and returned to the patient from the venous needle is collected from the arterial needle without passing trough patient's organs. Such blood-recirculation is not desirable because the purified blood is again extracorporeally circulated and, as a result, the volume of extracorporeal blood-circulation required to be purified is decreased so that purification efficiency is lowered.

A blood purification device (e.g. JP Patent Published 2000-502940) has been disclosed, in which blood-recirculation could be measured using a specific peak, as a benchmark, assigned within a variation of concentration of blood extracorporeally circulating by driving a ultrafiltration pump rapidly in a short period of time. Referring to the patent published, in the dialysis device disclosed, a sensor measuring blood concentration (hemoglobin concentration) was installed in the arterial blood circuit route and a recirculation of blood during dialysis treatment was determined with a specific peak detected by such as a sensor.

SUMMARY OF THE INVENTION

The object of the present invention is to provide a blood purification device for confirming whether a specific peak has been given by a blood concentration means or not, and detecting accurately a blood re-circulation by reducing parameters for calculating the blood-recirculation ratio.

A conventional blood purification device employs one sensor installed in the arterial blood circuit route to detect a blood concentration, and blood-recirculation is measured based on the variation of blood concentration, and accordingly when a specific peak is not provided because of some trouble on the ultrafiltration pump, a specific peak would not be measured by the sensor even if blood-recirculation had occurred. Therefore, a blood purification treatment could not be carried out efficiently.

Further, when a blood recirculation ratio of the blood flowing in the arterial blood circuit route was sought to be determined, a measured value (variation of blood concentration), a parameter for flowing blood in a blood pump, and a parameter of water removed were needed, and accordingly, error on the ratio would be large. Specifically, the more the parameters are needed for obtaining a ratio of blood-recirculation, the bigger the effect of parametric error and the lower the reliability of calculation.

An implementation of the present invention provides a blood purification device including: a blood circuit route having a arterial blood circuit route and a venous blood circuit route which circulate extracorporeally the blood collected from the patient; a blood pump provided to the arterial blood circuit route of the blood circuit route; a blood purifier that is connected between the arterial blood circuit route and the venous blood circuit route, for purifying the blood flowing in the blood circuit route; a blood concentration means for providing a specific peak within the variation of blood concentration by concentrating the blood rapidly; and a detecting means for detecting the specific peak provided by the blood concentration means. The blood purification device is adapted to measure re-circulating blood, of which the blood is returned to the patient from the venous blood circuit route and is introduced again to the arterial blood circuit route, based on the specific peak measured by the detecting means including the first detecting means installed in the arterial blood circuit route and the second detecting means installed in the venous blood circuit route.

An implementation of the present invention also provides a blood purification device that includes: a calculation means for calculating the proportion of the re-circulating blood flowing in the arterial blood circuit route and the venous blood circuit route by comparing the specific peaks measured by the first detecting means and the second detecting means.

Another implementation of the present invention provides a blood purification device that includes a hematocrit sensor provided as a first detecting means and a second detecting means for detecting hematocrit values of the blood flowing in the arterial blood circuit route and the venous blood circuit route.

Another implementation of the present invention provides a blood purification device that includes the second detecting means installed around the periphery of the blood purification means.

Another implementation of the present invention is a blood purification device that includes a blood concentration means which has a water removal means to remove water from the blood flowing in the blood purification means. The device measures a blood benchmark value based on the blood concentration of the patient and determines the optimal amount of water which should be removed based on the blood benchmark by the water removal means thereby controlling the variation in the blood concentration.

Another implementation of the present invention is a blood purification device including a blood purification means which has a dialyzer for introducing and passing out the dialysis fluid through the dialyzing membrane. The blood benchmark value can be obtained from the hematocrit value of the patient and the venous blood pressure flowing in the venous blood circuit route or the dialysis fluid pressure, which is a pressure of the dialysis fluid pushed out from the dialyzer.

According to an implementation of the present invention, a specific peak provided by the blood concentration means can be confirmed and a blood re-circulation can be accurately measured because of less parameters needed to obtain the ratio of re-circulation blood. Less parameters are needed because in addition to the first detecting means in the arterial blood circuit route the second detecting means in the venous blood circuit route is installed.

Further according to an implementation of the present invention, the detection of the re-circulating blood can be measured more precisely with less error than the device which obtains the ratio of the re-circulating blood based on a flowing volume of blood, volume of removed water and other parameters because the calculation means calculates the ratio of the re-circulating blood flowing in the arterial blood circuit route by comparing the specific peaks measured by the first detecting means and the second detecting means.

Further according to an implementation of the present invention, the specific peak can be measured in better way because the first detecting means and the second detecting means each have a hematocrit sensor.

According to the present invention, the specific peak provided by the water removal means can be measured earlier and the detection of the re-circulating blood can be carried out more precisely because the second detecting means is installed near the blood purification means.

Further according to the present invention, the re-circulation ratio can be measured by the volume of water removed corresponding to the patient's blood condition because the variation of the blood concentration is controlled by determining an optimal volume of water to be removed by the water removal means based on the blood benchmark, which is derived based on the patient's blood concentration.

DETAIL DESCRIPTION OF PREFERRED EMBODIMENTS

Figure 1:
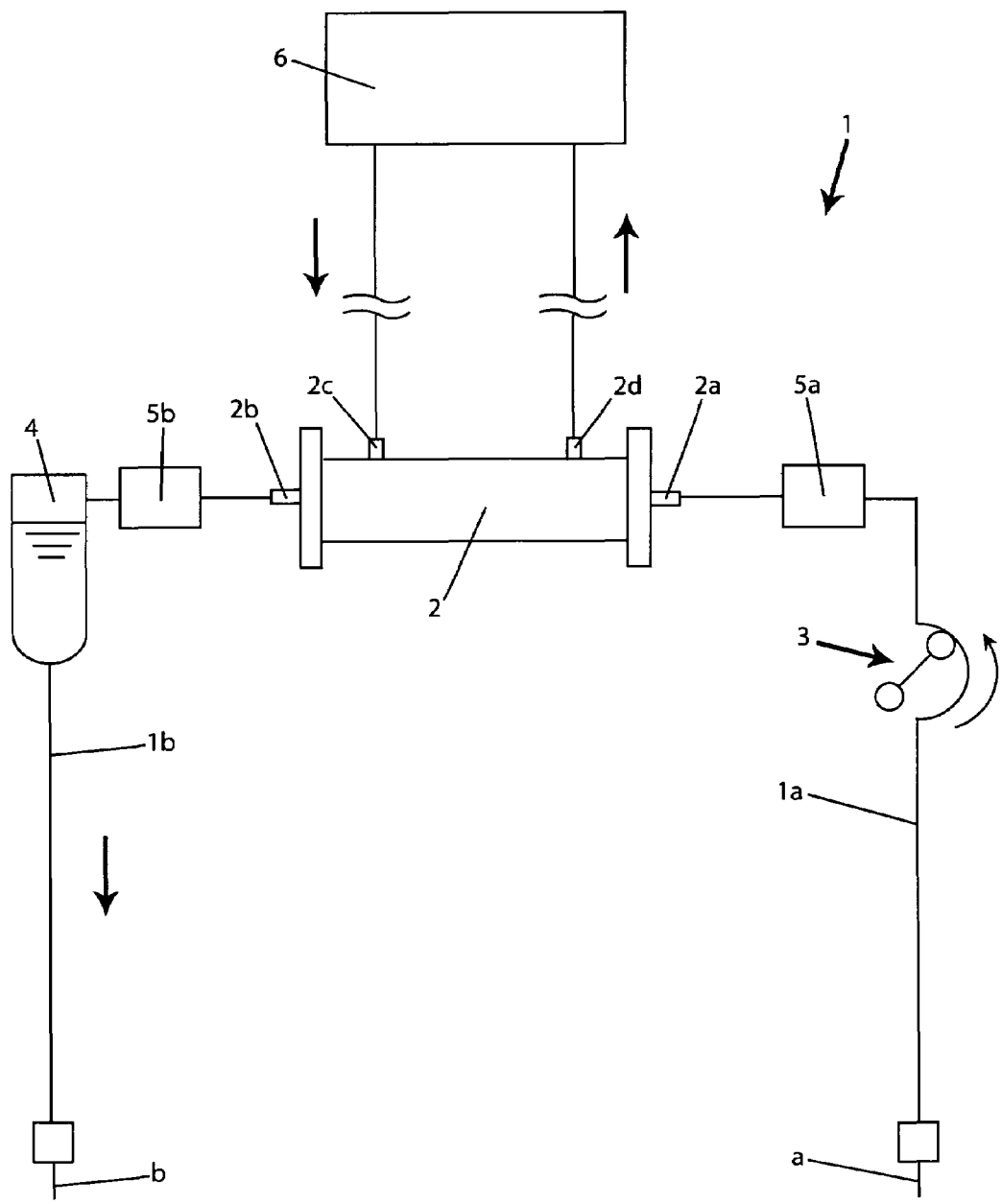
FIG. 1 is a schematic diagram of the blood purification device of the present invention.

The embodiments of the present invention are explained using figures. The blood purification device according to the present embodiments is a device to purify the patient's blood by extracorporeal circulation and is applied to a dialysis device which is used for a dialysis treatment. The dialysis device includes, as shown in FIG. 1, a blood circuit route attached dialyzer 2 as a blood purifier and dialysis device main body 6 supplying dialysis fluid to dialyzer 2 and removing water. Blood circuit route 1 includes mainly, as shown the same figure, arterial blood circuit route 1a and venous blood circuit route 1b, which are made from flexible tubing, and dialyzer 2 is installed between arterial blood circuit route 1a and venous blood circuit route 1b.

Arterial needle a is attached to the end of arterial blood circuit route 1a, and peristaltic pump 3 and first detecting means 5a are attached in the middle of arterial blood circuit route 1a. Venous needle b is attached to the end of venous blood circuit route 1b, and second detecting means 5b and drip chamber 4 to remove bubbles are attached in the middle of venous blood circuit route 1b.

When blood pump 3 is driven while arterial needle a and venous needle b are attached to the patient, the blood of the patient flows through arterial blood circuit route 1a and into dialyzer 2 which purifies the blood. The purified blood returns to the patient through venous blood circuit route 1b after air bubbles are removed in drip chamber 4. Thus, the blood of the patient is purified by dialyzer 2 during extracorporeally circulating through blood circuit route 1.

Several ports are located on the case of dialyzer 2; blood inlet port 2a, blood outlet port 2b, dialysis fluid inlet port 2c and dialysis fluid outlet port 2d. Blood inlet port 2a and blood outlet port 2b are connected to the end of arterial blood circuit route 1a and venous blood circuit route 1b, respectively. Dialysis fluid inlet port 2c and dialysis fluid outlet port 2d are connected to dialysis fluid inlet line L1 and dialysis fluid outlet line L2, respectively. Lines L1 and L2 extend from dialysis device main body 6.

The dialyzer includes multiple hollow fibers. The blood flows inside of the hollow fibers and the dialysis fluid flows between the outside surface of the hollow fibers and the inside surface of the dialyzer case. The hollow fibers include many micropores that are located in the outside and the inside surface of the hollow fiber membrane, and through which waste products in the blood are dialyzed to the dialysis.

Figure 2:
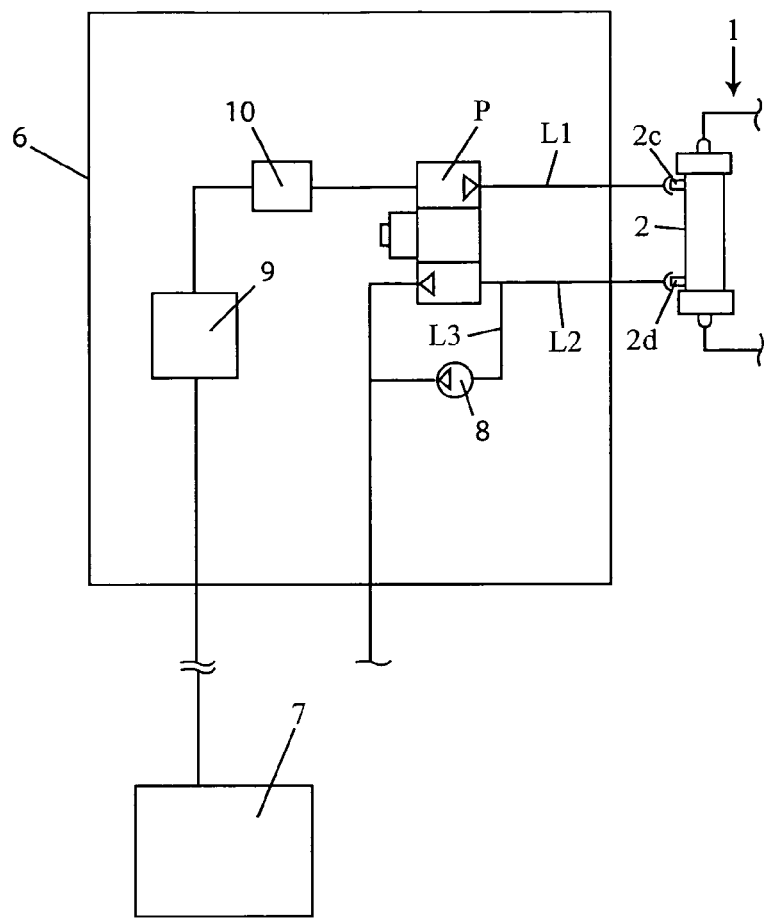
FIG. 2 is a schematic diagram of the dialysis device which is applied to the blood purification device of the present invention.

Further, as shown in FIG. 2, dialysis device main body 6 includes; duplex pump P that is connected between dialysis fluid inlet line L1 and dialysis fluid outlet line L2; bypass line L3 is connected to dialysis fluid inlet line L2 bypassing duplex pump P; and ultrafiltration pump 8 (blood concentration means) that is connected to bypass lines L3. Additionally, one end of dialysis fluid inlet line L1 is connected to dialyzer 2 (dialysis fluid inlet port 2c) and the other end is connected to dialysis fluid supplier 7 which prepares the dialysis fluid of the predetermined concentration.

One end of dialysis fluid outlet line L2 is connected to dialyzer 2 at dialysis fluid outlet port 2d. The other end of dialysis fluid outlet line L2 is connected to draining means (not shown in Fig.). The dialysis fluid supplied from dialysis fluid supplier 7 passes through dialysis fluid inlet line L1 to dialyzer 2, dialysis fluid outlet line L2 and bypass line L3, and is let out to the draining means. In FIG. 2, a heater 9 and a deaeration unit 10 are both connected to dialysis fluid inlet line L1.

Ultrafiltration pump 8 to concentrate the blood removes water from the blood of the patient flowing through dialyzer 2. When ultrafiltration pump 8 is activated, the volume of dialysis fluid let out of dialysis fluid outlet line L2 becomes greater than that of dialysis fluid introduced from dialysis fluid inlet line L1 because duplex pump P is quantitative; and water is removed from the blood by the difference of the inlet and outlet volume. Instead of ultrafiltration pump 8, other means (e.g. a balancing chamber) can be used to remove water from the blood of the patient.

Ultrafiltration pump 8 as a blood concentration means according to the present embodiment allows removing water rapidly in a short period of time. Specifically, the water removal during dialysis at a constant rate is temporally ceased (nevertheless extracorporeal blood circulation is continued) and when the hematocrit value measured becomes stable, ultrafiltration pump 8 is activated rapidly in a short period of time to remove water. The specific peak in accordance with a change of blood concentration (i.e. hematocrit value) during removing water can be provided. 'Rapidly in a short period of time' is equivalent to the scale and time which allows recognizing the pulse provided after passing the circuit and 'specific' is equivalent to a level which allows distinguishing its variation pattern from the pattern due to other factors due to such as the variation of the pump or the patient's movement.

Figure 3:
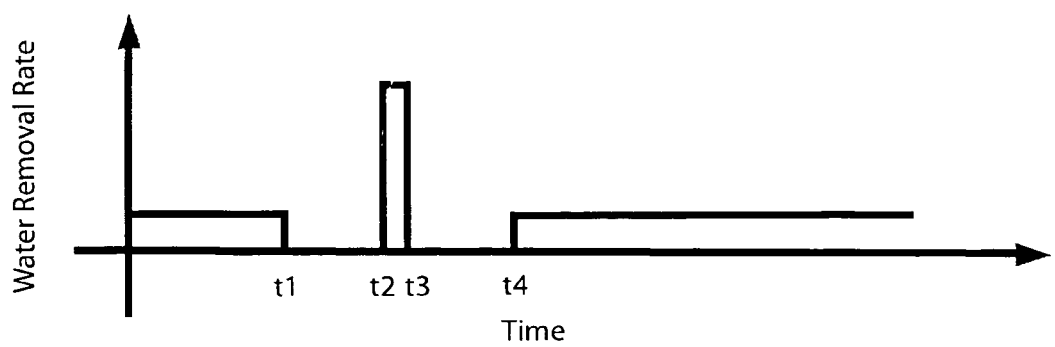
FIG. 3 is a graph which shows controlling the ultrafiltration pump of the blood purification device when the water removal is carried out rapidly in a short period of time.
Figure 4:
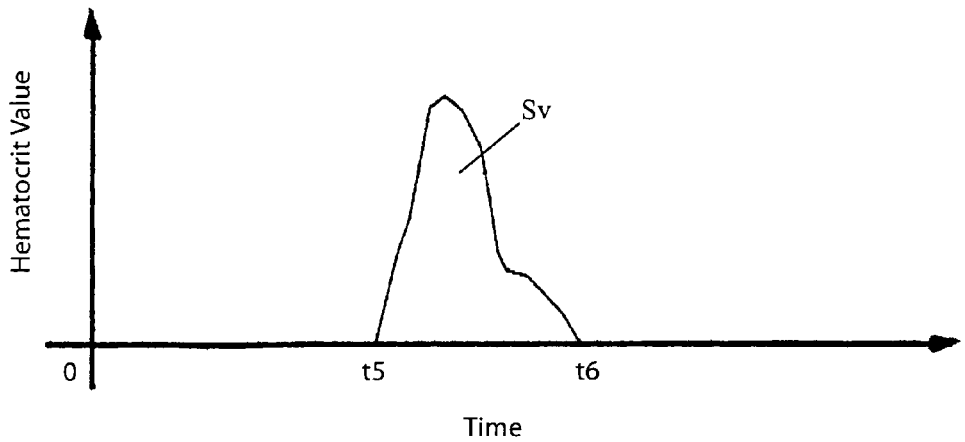
FIG. 4 is a graph which shows variation of hematocrit values measured by the second detecting means of the blood purification device.

More specifically, as shown in FIG. 3, the constant rate water removal (regular water removal) is ceased at time t1, and when the hematocrit being measured becomes stable at time t2, ultrafiltration pump 8 is activated at the higher rate than the regular rate until time t3. The interval between t2 and t3 is subtle. Therefore the rapider water removal in a less short period of time than regular water removal can be carried out. For example as shown in FIG. 4, the specific peak is provided in the hematocrit values.

First detecting means 5a and second detecting means 5b are attached to arterial blood circuit route 1a and venous blood circuit route 1b, respectively to measure the blood concentration, specifically hematocrit value, in the circuits. First detecting means 5a and second detecting means 5b include a hematocrit sensor. The hematocrit sensor contains a photo emitter, such as light emitting diode (LED) and a photo detector, such as a photo diode, and measure the hematocrit value that reflects the concentration of the patient's blood by emitting the light to the blood from the light emitting element and detecting the light transmitted or reflected at the light detecting element.

Specifically, the hematocrit value, which reflects the blood concentration, is obtained from the electronic signal output from the photo detector. The hematocrit value can be obtained by quantifying the red blood cells electronically optically based on the fact that blood components, such as red blood cells and plasma, have specific absorption spectra. More specifically, the near-infrared emitted from the photo emitter, which is absorbed and scattered when being reflected by the blood, is received by the photo detector. The light absorption and scattering coefficient is analyzed based on the intensity of the light measured by the photo detector and thereby used to calculate the hematocrit value.

Figure 5:
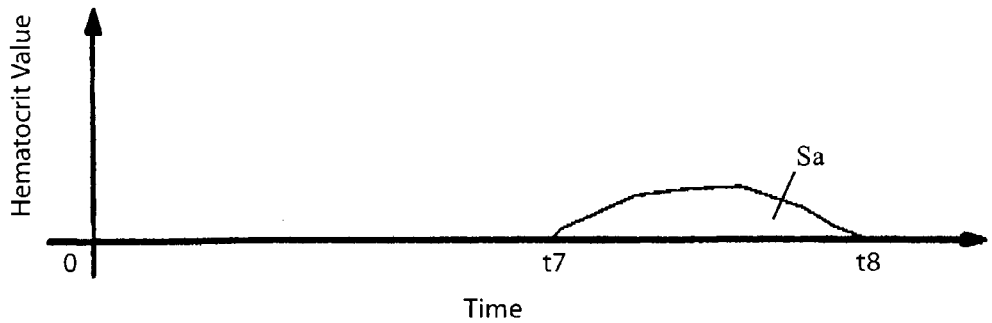
FIG. 5 is a graph which shows variation of hematocrit values measured by the first detecting means of the blood purification device, when the blood re-circulation occurs.

According to the above composition, first detecting means 5a detects the hematocrit value of the blood collected from the patient through arterial needle a while dialysis treatment because first detecting means 5a is attached to arterial blood circuit route 1a and second detecting means 5b measures the hematocrit value of the blood returned to the patient after purified by dialyzer 2 because second detecting means 5b is attached to venous blood circuit route 1b. Specifically, as shown in FIG. 4, firstly second detecting means 5b detects the specific peak provided by ultrafiltration pump 8 and secondary when the blood is re-circulated into arterial blood circuit route 1a, the remained specific peak in the re-circulated blood can be detected by first detecting means 5a as shown in FIG. 5.

Accordingly, second detecting means 5b allows confirming the specific peak provided by ultrafiltration pump 8 and first detecting means 5a allows detecting the blood re-circulation. Specifically, the device of the present embodiment allows detecting the blood re-circulation more certainly and more accurately than other device, in which a detecting means is attached only to an arterial blood circuit route, because the device of the present embodiment allows confirming the specific peak provided by ultrafiltration pump 8.

Figure 6:
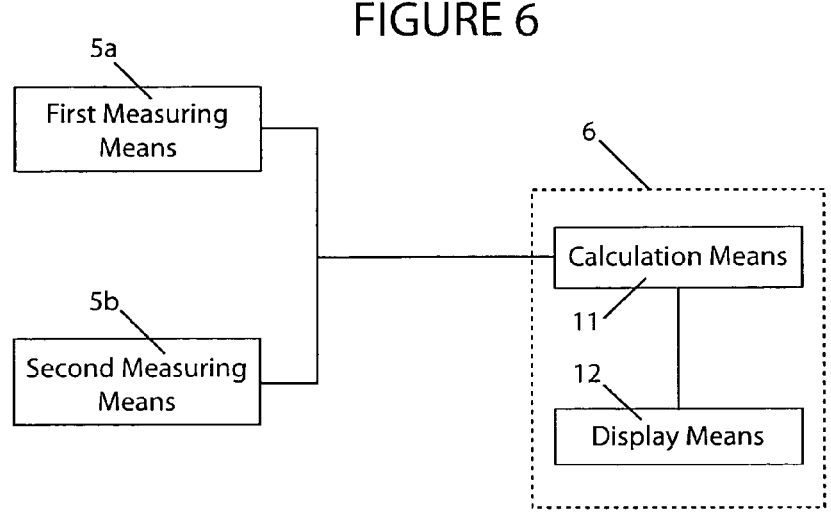
FIG. 6 is a block diagram which shows the connection relationship for the first detecting means, the second detecting means, the calculation means and the display means of the blood purification device.

Further, first detecting means 5a and second detecting means 5b, are electrically connected, as shown in FIG. 6, to calculation means 11 attached to dialysis device main body 6. Calculation means 11 is composed of such as a microcomputer and compares the hematocrit values (specific peaks) measured by first detecting means 5a and second detecting means 5b and allows calculating the ratio of the re-circulating blood flowing in arterial blood circuit route 1a.

Specifically, if the blood re-circulation occurs, the time (t5 in FIG. 4) from the time when ultrafiltration pump 8 provides the specific peak until the time (t7 in FIG. 7) when the blood reaches to second detecting means 5b is predicted. Calculation means 11 compares the hematocrit value measured by second detecting means 5b at time t5 after the specific peak was provided by ultrafiltration pump 8 and the hematocrit value measured by first detecting means 5a at time t7 after that.

Thus, as time t5 which allows the blood to reach to second detecting means 5b and time t7 which allows the blood after re-circulated to reach to first detecting means 5a are predicted, the phenomenon of heart-lung-re-circulation (purified blood only after passing the heart and lung without passing other tissues and organs is put out from the patient's body) and the re-circulation which should be measured become distinguishable. Further, instead of the above procedure, it would be acceptable that calculation means 11 allows detecting that the hematocrit values measured by first detecting means 5a and second detecting means 5b are beyond the predetermined value and then hematocrit values beyond the predetermined value are compared each other.

Then, variations of hematocrit values of first detecting means 5a and second detecting means 5b are obtained based on the relationship graph between time and hematocrit value as shown in FIGS. 4 and 5, and the areas of parts of time (varied parts) which should be compared each other are obtained by mathematical calculation such as integration method. For example, if the area of varied part measured by second detecting means 5b (from t5 to t6 in FIG. 4) is Sv and the area of varied part measured by first detecting means 5a (from t7 to t8) is Sa, the ratio of the re-circulation blood (re-circulation ratio) Rrec can be obtained from the following formula:

$$Rrec(\%) = (Sa/Sv) \times 100$$

The time of varied part measured by first detecting means 5a (time interval between t7 and t8) is set as longer than the time of varied time measured by second detecting means 5b (time interval between t5 and t6) because it should be considered that the blood to which the specific peak is provided is diffused during flowing from second detecting means 5b to first detecting means 5a. The obtained ratio of the re-circulation blood is displayed on display means 12 attached to dialysis device main body. Accordingly a medical worker such as medical doctor can see the result. If there is no blood re-circulation, Sa is 0 and the numbed displayed as the ratio of the re-circulation blood is 0 (%). Accordingly, the medical worker can see even the ratio in addition to occurrence of the blood re-circulation and can utilize such information for further treatment including such as re-punctuation of the needle to suppress the blood re-circulation and re-formation of the shunt.

Thus, the present invention allows measuring the blood re-circulation and more precisely with less error than other device which obtains the ratio of the blood re-circulation based on other parameters such as volume of the flowing blood or volume of the flowing water removed. Specifically, the volume of the flowing blood or removed water is generally obtained from the driving rate of the blood pump or the ultrafiltration pump, which may easily cause an error between the driving rate and the actual flowing volume. If such parameter is used to calculate the ratio of the blood re-circulation, the error could be bigger and damages its accuracy. In contrast, the present embodiment can suppress such error because it does not employ the flowing volume as a parameter.

Further, the burden to the patient can be suppressed and the blood re-circulation can be measured using the existing circuit without change such as an extracorporeal circuit, because the time to concentrate the blood and to measure the data is short. Not only an adverse effect, such as extension of dialysis time, during the treatment, but also a burden, such as physical and mental burdens, to the patient can be reduced because the measurement is only once during one dialysis treatment. Also, contamination and/or infection from the injection port can be prevented because no indicator, such as a benchmark, is required to be injected, and neither indicator injection port nor injection means is required because the addition of the benchmark to measure the blood re-circulation is carried out using existing dialyzer 2. Furthermore, an automatic measurement of the blood re-circulation also can be carried out, and by which, the deviation due to the medical worker can be lowered more than a manual measurement.

Further, the data measured by first detecting means 5a and second detecting means 5b can be compared without removing the water by using both measurement means and the correction can be automatically carried out. In addition, the water removal property of dialyzer 2 can be monitored because first detecting means 5a and second detecting means 5b are attached to the inlet and the outlet of dialyzer 2, respectively.

The specific peak provided by ultrafiltration pump 8 appears obviously as a variation of the hematocrit value. Therefore, if first detecting means 5a and second detecting means 5b are composed of a hematocrit sensor in accordance with the present embodiment, the detection of the instant specific peak can be carried out well and the measurement of the blood re-circulation can be carried out more precisely. Thus, the specific peak provided by ultrafiltration pump 8 can be measured much earlier because second detecting means 5b according to the present embodiment, as shown in FIG. 1, is attached nearby to dialyzer 2, so that the measurement of the blood re-circulation can be precisely carried out without an adverse effect due to a blood diffusion.

It is preferred that the optimal removal volume of water, including an optimal water removing rate; by ultrafiltration pump 8, which is a water removal means as a blood concentration means; is determined based on the blood benchmark obtained from the blood concentration of the patient, and then the variation of the blood concentration to measure the blood re-circulation is controlled. Specifically, when the specific peak in accordance with variation of the blood concentration is provided by concentrating the blood rapidly in a short period of time with ultrafiltration pump 8 to measure the blood re-circulation, the blood concentration, hematocrit value, may be overly increased, especially in the late stage of dialysis treatment. In order to prevent such adverse event, the optimal removal volume of the water, a removal volume of the water in accordance with the blood condition of the patient to prevent excessive increase of the blood concentration, is determined from the blood benchmark obtained based on the blood concentration of the patient who is taking the dialysis treatment, and then ultrafiltration pump 8 is activated to control the variation of the blood concentration when the blood concentration is carried out rapidly in a short period of time. Accordingly, the measure of the blood re-circulation can be carried out at will and at any time during the dialysis treatment.

The blood concentration, such as hematocrit value or hemoglobin concentration, of the patient; the venous blood pressure of the blood flowing in venous blood circuit route 1b, e.g. venous blood pressure obtained from air pressure of drip chamber 4; or the dialysis pressure of the dialysis fluid output from dialyzer 2, i.e. the liquid pressure of the dialysis fluid right after dialyzer 2 in dialysis fluid output line L2, can be employed as the blood benchmark of the patient.

Thus, the pressure difference between the blood passage and the dialysis fluid passage in dialyzer 2, the pressure difference between membranes which are hollow fiber membranes, i.e. dialysis membranes, is obtained from the difference of venous blood pressure and dialysis fluid pressure, which is considered as the blood benchmark that is the data to determined the optimal removal volume of the water which is the removal volume of the water in accordance with the patient's condition. In other word, the pressure difference between the above membranes varies depending on the blood concentration of the patient, flowing extracorporeally, and there it is the blood benchmark based on the blood concentration.

Specifically, if the measured blood concentration, including a blood concentration obtained from the pressure difference between membranes, of the patient is high, the variation of the blood concentration is set as small when the blood concentration is carried out rapidly in a short period of time, and if the measured blood concentration, including the same, is low, the activation of ultrafiltration pump 8 is controlled to increase the variation of the blood concentration and accordingly an excessive increase of the blood concentration of the patient can be prevented.

The present invention is not limited to the present embodiments. For example, if a means, e.g. a sensor measuring the hemoglobin concentration or a sensor measuring protein concentration, besides a hematocrit sensor, which can measure the specific peak provided with rapid water removal in a short period of time, can be employed as the first detecting means and the second detecting means. Further, the first detecting means and the second detecting means can be attached to any place of the arterial blood circuit route and the venous blood circuit route, respectively.

Further according to the present embodiment, although the ultrafiltration pump which can remove water rapidly in a short period of time is employed to provide a specific peak as a blood concentration means, any other means than the ultrafiltration pump capable to concentrate the blood can be employed. Further, according to the present embodiment, although the calculation means calculates the ratio of blood re-circulation (re-circulation rate), second detecting means 5*b* only confirms the specific peak provided or not and first detecting means 5*a* only measures the blood re-circulation so that the calculation means is not mandatory. Further, when the ratio of the blood re-circulation is out of the predetermined value range, an alert can be used to send a notice to a medical worker. Further, according to the present embodiment, dialysis device main body 6 is a dialysis monitoring device having no inside dialysis fluid supplier, but the present invention can be applied to a personal dialysis device including a inside dialysis fluid supplier.

Accordingly, a blood purification device having the first detecting means in the arterial blood circuit route and the second detecting means in the venous blood circuit route by which a specific peak provided by a blood concentration means can be detected can be applied to other medical device, such as a blood filtration treatment and a blood filtration-dialysis treatment, which is employed to circulates extracorporeally the blood and purify the blood for the medical treatment, or to a device having other function.

What is claimed is:

1. A blood purification device adapted to detect re-circulated blood flowing in said arterial blood circuit route, the re-circulated blood being blood that was returned to the patient from said venous blood circuit route but again directed to the arterial blood circuit route, the blood purification device comprising:
    a blood circuit route having an arterial blood circuit route and a venous blood circuit route to circulate extracorporeally the blood collected from a patient;
    a blood pump provided in said arterial blood circuit route;
    a blood purification means connected between said arterial blood circuit route and said venous blood circuit route, and purifies the blood flowing in said blood circuit route;
    a blood concentration means to provide a specific peak in blood concentration by concentrating the blood;
    a detecting means to detect the specific peaks in blood concentration provided by said blood concentration means, said detecting means further comprising a first detecting means provided to said arterial blood circuit route and a second detecting means provided to said venous blood circuit route; and
    a calculation means adapted for calculating a proportion of the re-circulated blood within the blood flowing in said arterial blood circuit route by comparing specific peaks in blood concentration detected by said first detecting means and said second detecting means.

2. A blood purification device of claim 1 comprising:
    said first detecting means and said second detecting means comprising a hematocrit sensor for measuring hematocrit values of the blood flowing in said arterial blood circuit route and said venous blood circuit route.

3. A blood purification device of claim 1 comprising;
    said second detecting means disposed nearby to said blood purification means.

4. A blood purification device of claim 1 comprising:
    said blood concentration means comprising a water removal means for removing water from the blood flowing in said blood purification means,
    said purification device being adapted to measure a blood benchmark based on the blood concentration of the patient and to control the variation of the blood concentration by determining an optimal removal volume of water by said water removal means based on said blood concentration benchmark.

5. A blood purification device of claim 4 comprising:
    said blood purification means comprising a dialysis device for inputting and outputting dialysis fluid through a dialysis membrane;
    said blood benchmark is a blood hematocrit value and derived from the venous blood pressure which is the blood pressure in said venous blood circuit route, or the dialysis fluid pressure which is the pressure of the dialysis fluid output from said dialyzer.

6. The blood purification device of claim 4, wherein the specific peak provided by
    said blood concentration means is provided by a blood concentration set in accordance with said blood benchmark.

7. The blood purification device of claim 1, wherein:
    said calculation means calculates the proportion of the re-circulated blood within the blood flowing in said arterial blood circuit route by comparing an area of the specific peak detected by said first detecting means over a first time period, during which the first detecting means detects a blood concentration in excess of a predetermined value, to an area of the specific peak detected by said second detecting means over a second time period, during which the second detecting means detects a blood concentration in excess of the predetermined value.

* * * * *